US006017694A

United States Patent [19]
Mak et al.

[11] Patent Number: 6,017,694
[45] Date of Patent: Jan. 25, 2000

[54] METHODS OF SCREENING FOR MODULATORS OF RESPIRATORY SYNCYTIAL VIRUS MATRIX PROTEIN INTERACTION

[75] Inventors: Paul Wai Mak, Pomona; Bryan Mark O'Hara, Pearl River, both of N.Y.

[73] Assignee: American Cyanamid Company, Madison, N.J.

[21] Appl. No.: 08/995,227

[22] Filed: Dec. 19, 1997

[51] Int. Cl.$^7$ .................................................. C12Q 1/70
[52] U.S. Cl. .................................. 435/5; 435/7.2; 435/7.9
[58] Field of Search ................................... 435/5, 7.2, 7.9

[56] References Cited

U.S. PATENT DOCUMENTS

| | | | |
|---|---|---|---|
| 4,615,974 | 10/1986 | Kingsman | 435/68 |
| 4,711,844 | 12/1987 | Yang | 426/5 |
| 4,745,057 | 5/1988 | Beckage et al. | 435/68 |
| 4,797,359 | 1/1989 | Finkelstein | 435/68 |
| 4,806,472 | 2/1989 | de Lovencourt et al. | 435/68 |
| 4,865,989 | 9/1989 | Hitzeman | 435/320 |
| 4,880,734 | 11/1989 | Burke et al. | 435/68 |

FOREIGN PATENT DOCUMENTS 0073657   3/1983   European Pat. Off. .

OTHER PUBLICATIONS

Chanock, R.M., Kim, H.W., Brandt, C.D. and Parrott, R.H., Viral infections of humans: epidemiology and control, pp. 471–489 (Evans, A.S., ed., 1982).
Cigan, M. and Donahue, T.F., (1987) Gene, 59:1–18.
Collins, P.L., et al., (1984) Proc. Natl. Acad. Sci. USA, 81:7683–7687.
Faaberg, K.S., and Peebles, M.E., (1988) Virology, 166:123–132.
Feilotter, H.E., et al., (1994) Nucleic Acids Res., 22:1502–1503.
Fleming, D. M. and Cross, K. W., (1993) Lancet, 342:1507–1510.
Glezen, W.P., et al., (1986) Am. J. Dis. Chil., 140:543–546.
Heggeness, M.H., et al., Proc. Natl. Acad. Sci. USA (1982), 79:6232–6236.
Holland and Holland, (1978) Biochemistry, 17:4900–4905.
Hitzeman, R., et al., (1980) J. Biol. Chem., 255:12073–12080.
Holberg, C.J., et al., (1991) Am. J. Epidemiol., 133:1135–1151.
Peeples, M. and Levine, S., (1979) Virol., 95:137–145.
Pringle, C.R., (1991) Arch Virol., 117:137–140.
Sanderson, C.M., et al., (1994) J. Virol., 68:69–76.
Satake, M. and Venkatesan, S., (1984) J. Virol., 50:92–99.
Stott, E. J. and Taylor, G., (1985) Arch. Virol., 84:1–52.
Sherman, F., et al., Methods in Yeast Genetics: A Laboratory Manual, pp. 113–115 (1992, Cold Spring Laboratory, NY).
Walsh, E.E. and Hruska, J., (1983) J. Virol., 47:171–177.
MacDonald, N.E. et al., (1982) New England J. Med., 307:397–400.
Wertz, G. W., et al. (1985) Proc. Natl. Acad. Sci. USA, 82:4075–4079.
Sanderson, C.M. et al., (1993) J. Virol., 67:651–663.
Sedlak, T.W., et al., (1995) Proc. Natl. Acad. Sci. USA, 92:7834–7838.
Markwell et al., Protein—protein interactions within paramyxoviruses identified by native disulfide bonding or reversible chemical cross–linking. J. Virol. 33(1):152–166, 1980.

*Primary Examiner*—Donna Wortman
*Attorney, Agent, or Firm*—Elizabeth M. Barnhard

[57] ABSTRACT

Methods of screening for modulators of respiratory syncytial virus matrix protein interaction are described. A host cell carrying a nucleic acid sequence encoding RSV matrix protein or fragments of RSV matrix protein which can bind to RSV matrix protein is cultured and the RSV matrix protein or RSV fragments are expressed. The interaction of the expressed RSV matrix protein or fragments is measured. A test sample is then added to the expressed RSV matrix protein or fragments and the effect of the test sample on RSV matrix protein interaction is measured.

22 Claims, 4 Drawing Sheets

FACTOR Xa TREATED MBP-M

SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
       (A) LENGTH: 28 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO:1:

Tyr Leu Glu Lys Glu Ser Ile Tyr Tyr Val Thr Thr Asn Trp Lys His
 1               5                  10                  15

```
Thr Ala Thr Arg Phe Ser Ile Lys Pro Leu Glu Asp
         20                  25
```

(2) INFORMATION FOR SEQ ID NO:2:

(i) SEQUENCE CHARACTERISTICS:
        (A) LENGTH: 51 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Val Tyr Asp Asn Lys Gly Ala Phe Lys Tyr Ile Lys Pro Gln Ser Gln
 1               5                  10                  15

Phe Ile Val Asp Leu Gly Ala Tyr Leu Glu Lys Glu Ser Ile Tyr Tyr
             20                  25                  30

Val Thr Thr Asn Trp Lys His Thr Ala Thr Arg Phe Ser Ile Lys Pro
             35                  40                  45

Leu Glu Asp
    50
```

(2) INFORMATION FOR SEQ ID NO:3:

(i) SEQUENCE CHARACTERISTICS:
        (A) LENGTH: 72 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

```
Phe Lys Asn Ala Ile Thr Asn Ala Lys Ile Ile Pro Tyr Ala Gly Leu
 1               5                  10                  15

Val Leu Val Ile Thr Val Tyr Asp Asn Lys Gly Ala Phe Lys Tyr Ile
             20                  25                  30

Lys Pro Gln Ser Gln Phe Ile Val Asp Leu Gly Ala Tyr Leu Glu Lys
             35                  40                  45

Glu Ser Ile Tyr Tyr Val Thr Thr Asn Trp Lys His Thr Ala Thr Arg
    50                  55                  60

Phe Ser Ile Lys Pro Leu Glu Asp
65                  70
```

(2) INFORMATION FOR SEQ ID NO:4:

(i) SEQUENCE CHARACTERISTICS:
        (A) LENGTH: 97 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

```
Ile Pro Thr Tyr Leu Arg Ser Ile Ser Val Lys Asn Lys Asp Leu Asn
 1               5                  10                  15

Ser Leu Glu Asn Ile Ala Thr Thr Glu Phe Lys Asn Ala Ile Thr Asn
             20                  25                  30

Ala Lys Ile Ile Pro Tyr Ala Gly Leu Val Leu Val Ile Thr Val Tyr
             35                  40                  45

Asp Asn Lys Gly Ala Phe Lys Tyr Ile Lys Pro Gln Ser Gln Phe Ile
    50                  55                  60
```

-continued

Val Asp Leu Gly Ala Tyr Leu Glu Lys Glu Ser Ile Tyr Tyr Val Thr
65                  70                  75                  80

Thr Asn Trp Lys His Thr Ala Thr Arg Phe Ser Ile Lys Pro Leu Glu
                85                  90                  95

Asp (2) INFORMATION FOR SEQ ID NO:5:

(i) SEQUENCE CHARACTERISTICS:
        (A) LENGTH: 143 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

Ala Cys Ser Leu Thr Cys Leu Lys Val Lys Ser Met Leu Thr Thr Val
1               5                   10                  15

Lys Asp Leu Thr Met Lys Thr Phe Asn Pro Thr His Glu Ile Ile Ala
                20                  25                  30

Leu Cys Glu Phe Glu Asn Ile Met Tyr Ser Lys Arg Val Ile Ile Pro
            35                  40                  45

Thr Tyr Leu Arg Ser Ile Ser Val Lys Asn Lys Asp Leu Asn Ser Leu
50                  55                  60

Glu Asn Ile Ala Thr Thr Glu Phe Lys Asn Ala Ile Thr Asn Ala Lys
65                  70                  75                  80

Ile Ile Pro Tyr Ala Gly Leu Val Leu Val Ile Thr Val Tyr Asp Asn
                85                  90                  95

Lys Gly Ala Phe Lys Tyr Ile Lys Pro Gln Ser Gln Phe Ile Val Asp
                100                 105                 110

Leu Gly Ala Tyr Leu Glu Lys Glu Ser Ile Tyr Tyr Val Thr Thr Asn
            115                 120                 125

Trp Lys His Thr Ala Thr Arg Phe Ser Ile Lys Pro Leu Glu Asp
    130                 135                 140

(2) INFORMATION FOR SEQ ID NO:6:

(i) SEQUENCE CHARACTERISTICS:
        (A) LENGTH: 167 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

Ile Ser Ala Asn Val Ser Leu Asp Glu Arg Ser Lys Leu Ala Tyr Asp
1               5                   10                  15

Val Thr Thr Pro Cys Glu Ile Lys Ala Cys Ser Leu Thr Cys Leu Lys
                20                  25                  30

Val Lys Ser Met Leu Thr Thr Val Lys Asp Leu Thr Met Lys Thr Phe
            35                  40                  45

Asn Pro Thr His Glu Ile Ile Ala Leu Cys Glu Phe Glu Asn Ile Met
50                  55                  60

Tyr Ser Lys Arg Val Ile Ile Pro Thr Tyr Leu Arg Ser Ile Ser Val
65                  70                  75                  80

Lys Asn Lys Asp Leu Asn Ser Leu Glu Asn Ile Ala Thr Thr Glu Phe
                85                  90                  95

```
Lys Asn Ala Ile Thr Asn Ala Lys Ile Ile Pro Tyr Ala Gly Leu Val
            100                 105                 110

Leu Val Ile Thr Val Tyr Asp Asn Lys Gly Ala Phe Lys Tyr Ile Lys
        115                 120                 125

Pro Gln Ser Gln Phe Ile Val Asp Leu Gly Ala Tyr Leu Glu Lys Glu
    130                 135                 140

Ser Ile Tyr Tyr Val Thr Thr Asn Trp Lys His Thr Ala Thr Arg Phe
145                 150                 155                 160

Ser Ile Lys Pro Leu Glu Asp
            165
```

(2) INFORMATION FOR SEQ ID NO:7:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

CGGAATTCAT GGAAACATAC GTGAACAAGC TT                          32

(2) INFORMATION FOR SEQ ID NO:8:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

AGGGCCCTAG GTTAATCCTC TAGTGGTTT                            29

(2) INFORMATION FOR SEQ ID NO:9:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

GGGAATGGAA ACATACGTGA ACAAGCTT                             28

(2) INFORMATION FOR SEQ ID NO:10:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

CGGGATCCTT AAACTGTGAT AACTAACACT A                           31

(2) INFORMATION FOR SEQ ID NO:11:

(i) SEQUENCE CHARACTERISTICS:
        (A) LENGTH: 31 base pairs (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:11:

CGGGATCCTT AGTAGGCACC AAGATCTACT A                                      31

(2) INFORMATION FOR SEQ ID NO:12:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:12:

CGGGATCCTT ATTCGGTGGT TGCTATATTT TC                                     32

(2) INFORMATION FOR SEQ ID NO:13:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:13:

CGGGATCCTT ATATTACTCT TTTTGATGTC AT                                     32

(2) INFORMATION FOR SEQ ID NO:14:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:14:

TTAGAAAAGA AATTG                                                        15

(2) INFORMATION FOR SEQ ID NO:15:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:15:

CGGGATCCTT AGATGAAATT ACTAGGCATT T                                      31

(2) INFORMATION FOR SEQ ID NO:16:

(i) SEQUENCE CHARACTERISTICS:
            (A) LENGTH: 25 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:16:

Ile Pro Thr Tyr Leu Arg Ser Ile Ser Val Lys Asn Lys Asp Leu Asn
1               5                   10                  15

Ser Leu Glu Asn Ile Ala Thr Thr Glu
            20                  25

METHODS OF SCREENING FOR MODULATORS OF RESPIRATORY SYNCYTIAL VIRUS MATRIX PROTEIN INTERACTION

FIELD OF THE INVENTION

This invention relates to methods of screening for modulators, including inhibitors or promoters, of respiratory syncytial virus matrix protein interaction.

BACKGROUND OF THE INVENTION

Human respiratory syncytial virus (RSV) is the most important viral agent responsible for severe respiratory tract disease among infants and children, resulting in approximately 100,000 hospitalizations and 5,000 deaths yearly in the United States (Chanock, R. M., Kim, H. W., Brandt, C. D. and Parrott, R. H., *Viral infections of humans: epidemiology and control*, pp. 471–489 (Evans, A. S., ed., 1982) (Plenum Publishing Corp., New York); Glezen, W. P., et al., (1986) Am. J. Dis. Chil. 140:543–546; MacDonald, N. E., et al., (1982) New England J. Med. 307:397–400; Stott, E. J. and Taylor, G., (1985) Arch. Virol., 84:1–52). Infants six weeks to nine months of age are most likely to develop bronchiolitis or pneumonia, with infants between two and seven months showing the peak incidence (Holberg, C. J., et al., (1991) Am. J. Epidemiol. 133:1135–1151).

About thirty percent of hospitalized young children with acute respiratory disease have RSV infection. In older children and adults the disease is milder. RSV appears to also be a major cause of morbidity and mortality in the elderly, equivalent to influenza. (Fleming, D. M. and Cross, K. W. (1993) Lancet 342:1507–1510). Infections with RSV are usually associated with fever, cough, runny nose, and fatigue, and are diagnosed clinically as bronchitis, bronchiolitis, pneumonia, croup, or viral infection. In older children and adults, the virus is generally limited to replication in the upper respiratory tract. Infants may be more severely involved when the virus extends into the lungs. Lung damage caused by RSV can be permanent.

RSV is a member of the order Mononegalovirales (Pringle, C. R., (1991) Arch. Virol. 117:137–140), which contains the families Paramyxoviridae, Rhabdoviridae, and Filoviridae. RSV belongs to the genus Pneumovirus of the Paramyxoviridae and exhibits the following structural characteristics. The genome consists of a nonsegmented, negative-sense RNA. This RNA is tightly wrapped in the viral proteins N (nucleocapsid protein), P (phosphoprotein), and L (polymerase), to form what is referred to as the nucleocapsid. The nucleocapsid is surrounded by a layer of M (matrix) proteins. This layer of M proteins is itself surrounded by a lipid membrane, in which the viral proteins G (glycoprotein), F (fusion), and SH (small hydrophobic) are embedded (Walsh, E. E. and Hruska, J., (1983) J. Virol., 47:171–177; Peeples, M. and Levine, S., (1979) Virol., 95:137–145).

Viral replication, in general, proceeds as follows. The glycoproteins in the viral membrane direct attachment of the virus to a target cell and direct fusion of the viral and cellular membranes. This is followed by dissociation (or uncoating) of the M proteins from the nucleocapsid and release of the nucleocapsid into the cell cytoplasm. Expression of the infecting nucleocapsid results in production of new nucleocapsids, and of M, G, F, and SH proteins. By a process which is poorly understood, the new nucleocapsids and M proteins become associated in regions of the target cell membrane in which the viral G, F, and SH proteins are embedded. This region of the cell membrane then buds, or pinches off, taking with it the nucleocapsid surrounded by M protein, and forms a new virion.

The exact intermolecular interactions which occur during the assembly of paramyxovirus virions in the infected cell is not known. It is believed that the M protein will be shown to play a central role in directing assembly of new virions, directing both its own self-assembly at the membrane and also colocalization of nucleocapsid and glycoprotein components. While there is no direct evidence of this for RSV, evidence supporting this belief has been generated for closely related viruses. In another paramyxovirus, Newcastle disease virus, the M protein can associate with membranes (Faaberg, K. S., and Peebles, M. E., (1988) Virology 166:123–132). The M protein of another paramyxovirus, Sendai virus, can self-associate (Heggeness, M. H., et al., Proc. Natl. Acad. Sci. USA (1982) 79:6232–6236). The M protein of the Sendai virus has also bee found in association with viral F protein in infected cells (Sanderson, C. M., et al., (1994) J. Virol. 68:69–76). These observations suggest that M protein of Sendai virus forms a bridge between nucleocapsids and glycoproteins located in the host cell membrane during virion assembly. This proposed model might also be applicable to other paramyxoviruses such as RSV.

Although the gene encoding RSV M protein had been cloned over a decade ago (Stake, M. and Venkatesan, S., (1984) J. Virol. 50:92–99), very little is known about the intermolecular interactions between M proteins or about the interaction of M protein with other RSV proteins. While it is believed that the M proteins of paramyxoviruses self-associate and mediate the association of nucleocapsids with nascent envelopes, it has not been known if RSV matrix proteins would physically interact directly in self-associating or if other proteins, cofactors, or processes were necessary to achieve this interaction. In particular, it was not known if the viral M2 protein (previously known as the 22K protein) played a role in the presumed interaction of the M protein with itself.

In order to combat the severe respiratory tract infections and disease in infants and children caused by RSV, there is a need to identify the protein—protein interactions of the RSV M protein and to develop a method for identifying compounds that modulate the M protein interactions to identify possible drug candidates to treat such severe infections. Compounds that inhibit M—M protein interaction may be effective antiviral agents if they prevent virus assembly. Compounds that promote M—M protein interaction may be effective antiviral agents if they prevent disassociation of matrix proteins after infection (uncoating).

For the first time, applicants have successfully expressed the RSV M protein in *E. coli* and yeast cells. Applicants have also purified the maltose binding protein-M fusion proteins for examination of protein—protein interaction in vitro and defined a specific protein—protein interaction between RSV M or fragments of the M protein in vivo. They have further demonstrated that the M protein, when fused separately with a transcription factor having a DNA binding domain and with the activation domain of a transcription factor, can interact within the complex milieu of a yeast cell in the absence of other viral proteins or unknown proteins or cofactors or processes supplied by the normal human cell host which are not supplied by the yeast cell host. Applicants have developed novel screening methods, including a novel high throughput yeast-based screening method (yeast two hybrid system), to identify agents that block or promote these specific protein—protein interactions. Agents identified by these new screening methods can be exploited as potential novel anti-RSV drugs with new modes of action. Additionally, the results provided by these novel screening methods will expand the understanding of the process of virus assembly which can be used to develop effective antiviral agents.

SUMMARY OF THE INVENTION

Figure 1A:
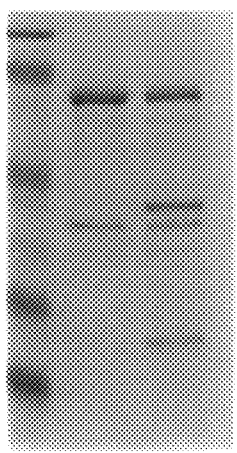
FIG. 1(A) is a 12% Coomassie blue stained SDS-PAGE gel of concentrated samples of affinity-purified MBP-M fusion protein in the absence of protease Factor Xa treatment (lane 1) or in the presence of Factor Xa treatment (lane 2).

The present invention is directed to a method of screening for modulators of RSV matrix protein interaction comprising the steps of:(a) culturing a host cell carrying a nucelic acid sequence encoding RSV matrix protein or fragments of RSV matrix protein which can bind to RSV matrix protein; (b) expressing the RSV matrix protein or fragments thereof in the cultured host cell of step (a); (c) measuring the interaction of the RSV matrix protein or fragments thereof expressed in step (b); and (d) adding a test sample to the expressed RSV matrix protein or fragments thereof of step (c) and measuring the effect on RSV matrix protein interaction. An increase in the RSV matrix protein interaction indicates the test sample promotes RSV matrix protein interaction and a decrease in the RSV matrix protein interaction indicates the test sample inhibits RSV matrix protein interaction.

The present invention is further directed to a method for screening for modulators of RSV matrix protein interaction comprising the steps of: (a) culturing yeast cells carrying: (1) a reporter construct comprising a promoter fused to an open reading frame encoding a reporter, (2) a gene encoding a transcription factor of the reporter of step (a)(1) having a DNA binding domain fused to a RSV matrix protein, and (3) a gene encoding a transcription factor for the reporter of step (a)(1) having an activation domain fused to a RSV matrix protein; (b) measuring the amount of expression of the reporter of step (a)(1) in the yeast cell culture of step (a), wherein an increase in the amount of expression of the reporter of step (a)(1) indicates the presence of RSV matrix protein interaction; and (c) adding a test sample to the yeast cell culture of step (b) and measuring the effect of the test sample on the amount of expression of the reporter of step (a)(1) in the yeast cell culture of step (b). Inhibition of the amount of expression of the reporter of step (a)(1) indicates the test sample inhibits RSV matrix protein interaction and enhancement of the amount of expression of the reporter of step (a)(1) indicates the test sample promotes RSV matrix protein interaction.

The present invention is also directed to an alternative method of screening for modulators of RSV matrix protein interaction comprising the steps of: (a) culturing yeast cells carrying: (1) a reporter construct comprising from one to eight copies of a LexA operon fused to a gene encoding lacZ, (2) a gene encoding the RSV matrix protein fused to the LexA DNA binding domain under the control of a full length ADH1 promoter, and (3) a gene encoding the RSV matrix protein fused to the B42 protein activation domain under the control of a GAL1 promoter in selective media; (b) measuring the effect on lacZ enzyme activity of the cultured yeast cells of step (a), wherein an increase in lacZ enzyme activity indicates the presence of RSV matrix protein interaction; and (c) adding a test sample to the yeast cell culture of step (b) and measuring the effect on lacZ enzyme activity. Inhibition of lacZ enzyme activity indicates the test sample inhibits RSV matrix protein interaction and enhancement of lacZ enzyme activity indicates the test sample promotes RSV matrix protein interaction.

Test samples which modulate RSV matrix protein interaction can be exploited as potential anti-RSV agents. An advantage of the present invention is that the effects of compounds on protein—protein interaction can be examined in a pure form in vitro without interference from other factors or cofactors. Further advantages of the present invention are that the effects of compounds on protein—protein interaction can be studied inside a living cell and the methodology can be adapted for high throughput robotic screening allowing for rapid screening of large numbers of compounds in an in vivo setting.

Upon further study of the specification and appended claims, further objects and advantages of this invention will become apparent to those skilled in the art.

DETAILED DESCRIPTION OF THE INVENTION

In the present invention, matrix protein derived from the 2B strain of RSV has been used; however, matrix protein from other RSV strains may be used. For example, the nucleotide sequence encoding matrix protein derived from RSV strain (A2) has 99% homology compared to the nucleotide sequence encoding the matrix protein of the RSV 2B strain (Satake, M. and Venkatesan, S., (1984) J. Virol., 50:92–99). The gene encoding the RSV matrix protein may be obtained by polymerase chain reaction using the RSV 2B viral genome as a template as described more fully in Example 1 or by using as templates the genes encoding RSV matrix protein from other RSV strains such as the A2 strain. Other known techniques for cloning or isolating genes may also be used. Accordingly, as used herein, the term RSV matrix protein refers to the aforementioned proteins or any fragments, derivatives, or other modifications thereof or any RSV matrix protein or fragment demonstrating at least about 40% homology thereto.

Preferably, the gene encoding the RSV matrix protein should be engineered to possess an EcoRI and BamHI restriction site at the 5' and 3' ends, respectively, with an in frame stop codon in front of the BamHI site. The gene is then inserted into the EcoRI and BamHI restriction sites of an expression vector containing a gene encoding a maltose binding protein for the expression of an in frame maltose binding protein-M fusion. Such an expression vector, designated pMAL-c, is commercially available from New England Biolabs, Beverly, Mass. The resulting fusion construct can then be used to transform *E. coli*. The transformed *E. coli* can then be used to express RSV matrix protein as a maltose binding protein fusion.

The expressed maltose binding fusion protein can be purified using an amylose affinity column and further purified by size exclusion chromatography. Preferably, extracts of the fusion protein are loaded onto an amylose affinity column containing an appropriate column buffer. The column is washed to remove unbound fractions and the fusion protein is then eluted stepwise from the column to yield purified fusion protein with yields as high as 80%.

The terms "DNA", "nucleotide sequence", and "nucleic acid sequence" are used interchangeably and are meant to include all forms of linear polymers comprising nucleotide bases, without limitation, including RNA when appropriate.

The term "upstream" is used herein to refer to the direction of transcription, with a sequence which is 5' to the transcribed sequence being referred to as "upstream".

The term "heterologous" refers to DNA sequences, proteins, and other materials originating from organisms other than the host cell (e.g., mammalian, avian, amphibian, insect, plant, yeast, viral) or combinations thereof not naturally found in the host cell.

Heterologous DNA sequences are expressed in a host by means of an expression "construct" or "vector". An expression vector is a replicable DNA construct in which a DNA sequence encoding the heterologous DNA sequence is operably linked to suitable control sequences capable of affecting the expression of a protein or protein subunit coded for by the heterologous DNA sequence in the intended host. Generally, eukaryotic control sequences include a transcriptional promoter, however, it may be appropriate that a sequence encoding suitable mRNA ribosomal binding sites be provided, and (optionally) sequences which control the termination of transription. Vectors useful for practicing the present invention include plasmids, viruses (including the bacteriophage), and integratable DNA fragments (i.e., fragments integratable into the host genome by genetic recombination). The vector may replicate and function independently of the host genome, as in the case of a plasmid, or may integrate into the genome itself, as in the case of an integratable DNA fragment. Suitable vectors will contain replicon and control sequences which are derived from species compatible with the intended expression host. For example, a promoter operable in a host cell is one which binds the RNA polymerase of that cell, and a ribosomal binding site operable in a host cell is one which binds the endogenous ribosomes of that cell.

DNA regions are operably associated when they are functionally related to each other. For example, a promoter is operably linked to a coding sequence if it controls the transcription of the sequence; a ribosome binding site is operably linked to a coding sequence if it is positioned so as to permit translation. Generally, operably linked means contiguous and, in the case of leader sequences, contiguous and in reading phase.

Transformed host cells are cells which have been transformed or transfected with the vectors constructed using recombinant DNA techniques and express the protein or protein subunit coded for by the heterologous DNA sequences. Yeast cells are preferably used as host cells in the present invention. A variety of yeast cultures, and suitable rexpression vectors for transforming yeast cells, are known. See, e.g., U.S. Pat. Nos. 4,745,057; 4,797,359; 4,615,974; 4,880,734; 4,711,844; and 4,865,989. *Saccharomyces cerevisiae* is the most commonly used among the yeasts, although a number of other yeast species are commonly available. See, e.g., U.S. Pat. No. 4,806,472 (*Kluveromyces lactis* and expression vectors useful therein). Standard procedures for growth and transformation of yeast cells such as the procedures described in Sherman, F., et al., *Methods in Yeast Genetics: a Laboratory Manual*, (1992, Cold Spring Harbor Laboratory, NY) can also be used. Yeast vectors may contain an origin of replication from the endogenous 2 micron yeast plasmid or an autonomously replicating sequence (ARS) which confers on the plasmid the ability to replicate at high copy number in the yeast cell, centromeric (CEN) sequences which limit the ability of the plasmid to replicate at only low copy number in the yeast cell, a promoter, DNA encoding the heterologous DNA sequences, sequences for polyadenylation and transcription termination, and a selectable marker gene. Exemplary plasmids and detailed materials and methods for making and using same are in the Examples section.

When yeast cells are used as the host cells, any prmoter capabhle of functioning in yeast systems may be selected for use in the constructs and cells used in the present invention. Suitable promoting sequences in yeast vectors include the promoters for metallothionein, 3-phosphoglycerate kinase (Hitzeman, R., et al., (1980) J. Biol. Chem. 255: 12073), or other glycolytic enzymes (Holland et al., (1978) Biochemistry 17:4900), such as enolase, glyceraldehyde-3-phosphate dehydrogenase, hexokinase, pyruvate, decarboxylase, phosphofructofinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further described in R. Hitzeman et al., European Patent Application No. 0073657. Other promoters, which have the additional advantage of transcription controlled by growth conditions, are the promoter regions for alcohol dehydrogenase, 1,2,-isocytochrome C, acid phosphates, degradative enzymes associated with nitrogen metabolism, and the aforementioned metallothionein and glyceraldehyde-3-phosphate dehydrogenase, as well as enzymes responsible for maltose and galactose utilization, such as the galactose inducible promoter, GAL1. Finally, in constructing suitable expression plasmids, the termination sequences associated with these genes may also be ligated intot he expression vector 3' of the heterologous coding sequences to provide polyadenylation and termination of the mRNA. In preparing the preferred expression vectors for use in the present invention, translational initiation sites are chosen to confer the most efficient expression of a given nucleic acid sequence in the yeast cell. See, Cigan, M. and Donahue, T. F., (1987) Gene, 59:1–18, for a description of suitable translational initiation sites.

In certain preferred embodiments employing yeast cells transformed to express RSV matrix protein, an overnight yeast culture is diluted (1:5) with appropriate medium and incubated for 2 to 3 hours at 30° C. until the optical density (OD) at 600 nm is approximately 0.6 to 0.7. The yest cells are washed with 0.1M lithium acetate (LiAc) and resuspended in the same solution. After an incubation at 30° C. for one hour, cells are collected and resuspended in 0.5 ml of 0.1M LiAc. An aliquot of cells (50 ul) is mixed with 2 to 3 μg of yeast expression plasmids and incubated for 10 minutes at 30° C. Subsequently, 0.5 ml of 40% polyethylene glycol (PEG4000) is mixed with yeast cells and incubated of one hour at 30° C. Cells are then heat shocked for 10 minutes at 42° C. followed by washign and resuspending in 0.1 ml sterile distilled water. The final cell suspension is then plated onto synthetic dropout medium and incubated for 2 to 3 days until transformants appear. The growth of these transformed yeast cells in culture is measured by the ability of transformants to grow on selective media [-histidine] or the ability of transformed yeast cells to produce β-galactosidase. An increase in growth of the transformants or an increase in β-galactosidase indicates the presence of RSV matrix protein interaction.

The present invention provides methods of screenign test samples to identify modulators of RSV matrix protein interaction. A modulator of RSV matrix protein interaction will either increase or promote RSV matrix interaction or will decrease or inhibit RSV matrix interaction. A test sample may be a peptide, peptide fragments or a non-peptide. The non-peptide test sample may include chemical compounds, complexes, and salts, as well as natural product samples such as plant extracts or materials obtained from fermentation broths.

Prior to the present invention, there were no such screening methods because it was not known if matrix proteins from RSV or other paramyxoviruses physically interacted or, if they did, if other proteins, cofactors or processes were necessary to achieve an interaction between the matrix proteins. For the first time, a physical interaction between the matrix proteins of RSV and between fragments of the matrix protein of RSV have been demonstrated using purified matrix (M) protein. Additionally, for the first time, a physical interaction of RSV matrix proteins has been demonstrated to occur in yeast cells when the matrix protein is fused separately with the binding domain of a transcription factor, such as GAL4 DNA binding domain or LexA DNA-binding domain, and with the activation domain of a transcription factor, such as GAL4 activation domain or the B42 protein activation domain. For the first time, the present invention provides methods to screen for modulators of RSV matrix protein interaction.

In one method of the present invention, a host cell is cultured which carries a nucleic acid sequence encoding the RSV matrix protein or fragments of RSV matrix protein which can bind to RSV matrix protein. The RSV matrix protein or fragments are expressed in the cultured host cell and the interaction of the expressed RSV matrix protein or fragments is measured. A test sample is then added to the expressed RSV matrix protein or fragments and the effect of the test sample on the RSV matrix protein interaction is measured. An increase in the RSV matrix protein interaction indicates the test sample promotes RSV matrix protein interaction and a decrease in the RSV matrix protein interaction indicates the test sample inhibits RSV matrix protein interaction.

The nucleic acid sequence carried by the host cell may encode RSV matrix protein or fragments of RSV matrix protein which can bind to RSV matrix protein fused to a protein selected from the group consisting of maltose binding protein (MBP) and gluthathione-S-transferase.

In another embodiment, the nucleic acid sequence carried by the host cell encodes RSV matrix protein fused to MBP. The RSV matrix protein interaction is measured in this embodiment by first measuring the amount of formation of monomers and dimers of the fusion RSV matrix protein-MBP and then adding and measuring the effect of a test sample on the amount of formation of monomers and dimers. An increase in the amount of monomers indicates the test sample inhibits RSV matrix protein interaction.

In another method of the present invention, yeast cells are cultured which carry: (1) a reporter construct comprising a promoter fused to an open reading frame encoding a reporter, (2) a gene encoding a transcription factor for the reporter of the reporter construct having a DNA binding domain fused to a RSV matrix protein, and (3) a gene encoding a transcription factor for the reporter of the reporter construct having an activation domain fused to a RSV matrix protein. The amount of expression of the reporter in the yeast cell culture is measured. An increase in the amount of expression of the reporter indicates the presence of RSV matrix protein interaction. A test sample is then added to the yeast cell culture and the effect of the test sample on the amount of expression of the reporter in the yeast cell culture is measured. Inhibition of the amount of expression of the reporter indicates the test sample inhibits RSV matrix protein interaction and enhancement of the amount of expression of the reporter indicates the test sample promotes RSV matrix protein interaction.

The yeast cells are preferably *Saccharomyces cerevisiae* and, more preferably, are *Saccharomyces cerevisiae* strain HF7c (MATa ura3-52, his3-200, lys2-801, ade2-101, trp1-901, leu2-3, 112 gal4-542, gal80-538, LYS2::GAL1UAS-HIS3, URA3::GAL4-lacZ) (Feilotter, H. E., et al., (1994) Nucleic Acids Res., 22:1502–1503). The yeast cells designated *Saccharomyces cerevisiae* GBT-M+GAD-M (ATCC Accession No. 74401) are most preferred.

The promoter in the reporter construct preferably comprises a GAL1 promoter, described in Feilotter, H. E., et al., (1994) Nucleic Acids Res., 22: 1502–1503, or another promoter specific for a transcription factor having a binding domain. For expression of the fusion proteins, any suitable yeast promoters can be used, such as the ADH1 promoter described in Feilotter, H. E., et al., (1994) Nuceleic Acids Res., 22:1502–1503. The reporter construct perferably comprises a GAL1 promoter fused to a gene encoding His3 which is defined as a reporter construct comprising three copies of the GAL4 17-mer consensus sequences and the TATA of CYC1 promoter fused to lacZ. When the reporter construct comprises a GAL1 promoter fused to a gene encoding His3, then the gene encoding a transcription factor of the reporter of the reporter construct having a DNA binding domain fused to a RSV matrix protein preferably encodes a GAL4 DNA binding domain fused to the RSV matrix protein, and the gene encoding a transcription factor for the reporter of the reporter construct having an activation domain fused to a RSV matrix protein preferably encodes a GAL4 activation domain fused to the RSV matrix protein.

Figure 5:
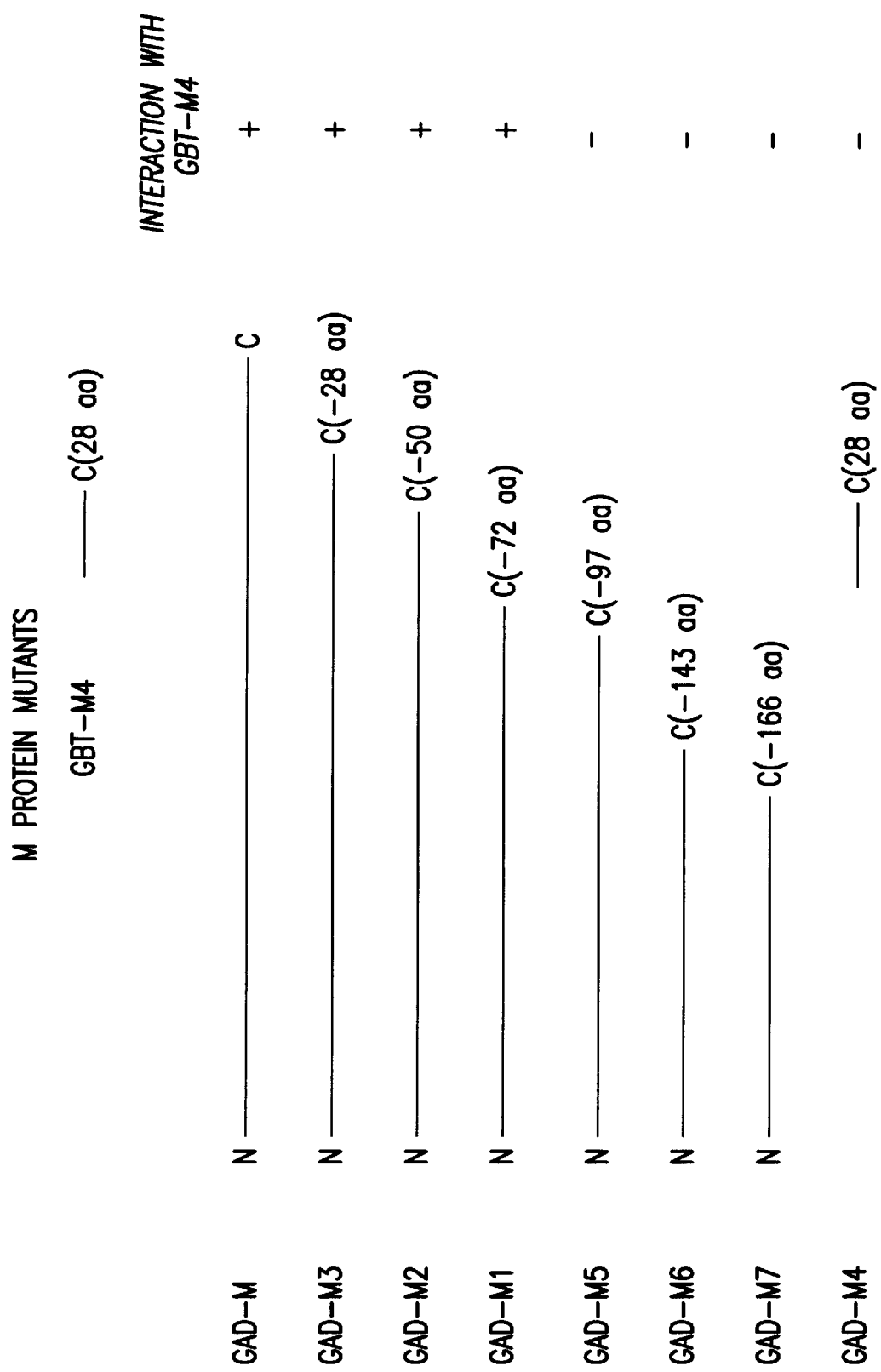
FIG. 5 is a domain map of the M—M protein interaction in a yeast two hybrid assay. GBT-M4 is a fusion construct containing GAL-4 DNA binding domain fused to the last twenty-eight amino acids of the M matrix protein C-terminus. GAD-M is a fusion construct containing GAL-4 activation domain fused to the M matrix protein. GAD-M3, GAD-M2, GAD-M1, GAD-M5, GAD-M6, GAD-M7, and GAD-M4 are fusion constructs containing the GAL-4 activation domain fused to M matrix protein mutants in which amino acids have been deleted from the matrix protein C-terminus as indicated in FIG. 5. Yeast strains were transformed with GBT-M4 and each of the fusion constructs and each of these double transforming yeast strains were tested for their growth phenotypes on selective medium lacking tryptophan, leucine and histidine. If the yeast strain was able to grow on this medium, it was interpreted as positive (+) for protein—protein interaction. If the yeast strain was unable to grow on this medium, it was interpreted as negative (31) for protein—protein interaction.

The gene encoding a transcription factor for the reporter of the reporter construct having a DNA binding domain fused to a RSV matrix protein preferably encodes a GAL4 DNA binding domain fused to the RSV matrix protein, and is more preferably on an expression vector designated GBT-M (ATCC Accession No. 98327). In an alternative of this preferred embodiment, the gene can encode the GAL4 DNA binding domain fused to a twenty-eight amino acid C-terminal fragment of the RSV matrix protein. The twenty-eight amino acid C-terminal fragment of the RSV matrix protein preferably comprises the amino acid sequence Tyr-Leu-Glu-Lys-Glu-Ser-Ile-Tye-Tye-Val-The-Thr-Asn-Trp-Lys-His-Thr-Ala-Thr-Arg-Phe-Ser-Ile-Lys-Pro-Leu-Glu-Asp hereinafter referred to as SEQ ID NO: 1. In another alternative of this preferred embodiment, the gene can encode the GAL4 DNA binding domain fused to a fragment of the RSV matrix protein having a C-terminal deletion which can bind to the twenty-eight amino acid C-terminal fragment of the RSV matrix protein encoded by the gene which encodes a transcription factor for the reporter of the reporter construct having an activation domain fused to a twenty-eight amino acid C-terminal fragment of the RSV matrix protein. The fragment of the RSV matrix protein having a C-terminal deletion which can bind to the twenty-eight amino acid C-terminal fragment of the RSV matrix protein is preferably selected from the group consisting of RSV matrix protein fragments designated GAD-M3, GAD-M2, GAD-M1, GAD-M5, GAD-M6, and GAD-M7 which are shown in FIG. 5. The number of C-terminal amino acids deleted from the RSV matrix protein, starting at the first C-terminal amino acid, are, respectively, twenty-eight (GAD-M3), fifty (GAD-M2), seventy-two (GAD-M1), ninety-seven (GAD-M5), one hundred forty-three (GAD-M6), and one hundred sixty-seven (GAD-M7). The amino acid sequences to be deleted from the RSV matrix protein to construct GAD-M3, GAD-M2, GAD-M1, GAD-M5, GAD-M6, and GAD-M7 are provided in the Sequence Listing as, respectively, SEQ ID NO: 1, SEQ ID NO: 2, SEQ ID NO: 3, SEQ ID NO: 4, SEQ ID NO: 5, and SEQ ID NO: 6.

Additionally, in this preferred embodiment, the gene encoding a transcription factor for the reporter of the reporter construct having an activation domain fused to a RSV matrix protein preferably encodes a GAL4 activation domain fused to the RSV matrix protein and is more preferably on an expression vector designated GAD-M (ATCC Accession No. 98326). In an alternative of this preferred embodiment, the gene can encode the GAL4 activation domain fused to a fragment of the RSV matrix protein having a C-terminal deletion which can bind to the twenty-eight amino acid C-terminal fragment of the RSV matrix protein encoded by the gene which encodes a transcription factor for the reporter of the reporter construct having a DNA binding domain fused to a RSV matrix protein. The fragment of the RSV matrix protein having a C-terminal deletion which can bind to the twenty-eight amino acid C-terminal fragment of the RSV matrix protein is preferably selected from the group consisting of RSV matrix protein fragments designated GAD-M3, GAD-M2, GAD-M1, GAD-M5, GAD-M6, and GAD-M7 which are shown in FIG. 5 and defined above. In another alternative of this preferred embodiment, the gene encodes the GAL4 activation domain fused to a twenty-eight amino acid C-terminal fragment of the RSV matrix protein which is preferably the twenty-eight amino acid sequence of SEQ ID NO: 1.

In a third embodiment of the present invention, yeast cells, which are cultured in selective media, carry: (1) a reporter construct comprising from one to eight copies of the LexA operon fused to a gene encoding lacZ, (2) a gene encoding the RSV matrix protein fused to the LexA DNA binding domain under the control of a full length ADH1 promoter, and (3) a gene encoding the RSV matrix protein fused to the B42 protein activation domain under the control of a GAL1 promoter. The effect on lacZ enzyme activity of the cultured yeast cells is measured. An increase in lacZ enzyme activity indicates the presence of RSV matrix protein interaction. A test sample is then added to the yeast cell culture and the effect of the test sample on lacZ enzyme activity is measured. A decrease in lacZ enzyme activity indicates the test sample inhibits RSV matrix protein interaction and an increase in lacZ enzyme activity indicates the test sample promotes RSV matrix protein interaction.

The cultured yeast cells are preferably *Saccharomyces cerevisiae* and, more preferably, are *Saccharomyces cerevisiae* strain HF7c (MATa ura3-p52, his3-200, lys2-801, ade2-101, trp1-901, leu2-3, 112 gal4-542, gal80-538, LYS2::GAL1UAS-HIS3, URA3::GAL4-lacZ) (Feilotter, H. E., et al., (1994) Nucleic Acids Res., 22:1502–1503). The yeast cells designated *Saccharomyces cerevisiae* LexA-M+ pB40-M+1 and 2 (ATCC Accession No. 74400) are most preferred.

The gene encoding the RSV matrix protein fused to the LexA DNA binding domain under the control of a full length ADH1 promoter is preferably on an expression vector designated LexA-M (ATCC Accession No. 98322).

The gene encoding the RSV matrix protein fused to the B42 protein activation domain under the control of a GAL1 promoter is preferably on an expression vector designated pB42-M (ATCC Accession No. 98323).

The selective media preferably lacks histidine.

In a preferred method of screening for modulators of RSV matrix protein interaction, the first step comprises culturing yeast cells in media in the absence of histidine. The cultured yeast cells carry the following: (1) a reporter construct having a GAL1 promoter fused to a gene encoding His3 or, alternatively, a reporter construct which contains three copies of the GAL4 17-mer consensus sequences and the TATA of the CYC1 promoter fused to the lacZ which is integrated into the yeast genome (available from the Clontech MATCHMAKER™ LexA two hybrid system, Clontech Laboratories, Inc., Palo Alto, Calif.); (2) a gene encoding the GAL4 DNA binding domain fused to the RSV matrix protein; and (3) a gene encoding the GAL4 activation domain fused to the RSV matrix protein.

The first gene is expressed in a yeast two hybrid expression plasmid such as pGBT$_9$ which is described in Feilotter, H. E., et al., (1994) Nucleic Acids Res., 22: 1502–1503. The nucleic acid sequence which encodes the RSV matrix protein is inserted into the EcoRI and BamHI restriction sites of the yeast two hybrid expression plasmid to make an expression plasmid that expresses an in frame fusion protein of RSV matrix protein fused to the GAL4 DNA-binding domain. A sample of *E. coli* (DH5α) containing the first nucleic acid sequence encoding the RSV matrix protein fused to the GAL4 DNA-binding domain in accordance with the present invention, designated *E. coli* DH5α GBT-M, has been deposited under the terms of the Budapest Treaty with the American Type Culture Collection (ATCC) at 12301 Parklawn Drive, Rockville, Md. 20852 USA under Accession Number ATCC 98327.

The first nucleic acid sequence may encode a twenty-eight amino acid C-terminal fragment of the RSV matrix protein fused to the GAL4 DNA binding domain. The twenty-eight amino acid C-terminal fragment of the RSV matrix protein fused to the GAL4 DNA binding domain may comprise the amino acid sequence of SEQ ID NO: 1.

The second nucleic acid sequence is expressed in a yeast two hybrid expression plasmid such as pGAD$_{424}$ which is described in Feilotter, H. E., et al., (1994) Nucleic Acids Res., 22: 1502–1503. The nucleic acid sequence which encodes the RSV matrix protein is inserted into the EcoRI and BamHI restriction sites of the yeast two hybrid expression plasmid to make an expression plasmid that expresses an in frame fusion protein of RSV matrix protein fused to the GAL4 activation domain. A sample of E. coli (DH5α) containing the second nucleic acid sequence encoding the RSV matrix protein fused to the GAL4 activation domain in accordance with the present invention, designated E. coli DH5α GAD-M, has been deposited under the terms of the Budapest Treaty with the American Type Culture Collection (ATCC) at 12301 Parklawn Drive, Rockville, Md. 20852 USA under Accession Number ATCC 98326.

The second nucleic acid sequence may encode a fragment of the RSV matrix protein from which a portion of the C-terminal end of the RSV matrix protein has been deleted, fused to the GAL4 activation domain. The fragment of the RSV protein is preferably selected from the group consisting of fragments designated GAD-M3, GAD-M2, GAD-M1, GAD-M5, GAD-M6, and GAD-M7 which are shown in FIG. 5 and defined earlier in this application.

In the next step of this preferred method, the growth of the yeast cells in culture is measured as described earlier with an increase in growth indicating the presence of RSV matrix protein interaction. In the final step, a test sample is added to the yeast cell culture and the effect on growth is measured. Inhibition of growth indicates the test sample inhibits RSV matrix protein interaction and enhancement of growth indicates the test sample promotes RSV matrix protein interaction.

In an alternative preferred method of screening for modulators of RSV matrix protein interaction, the first step comprises culturing yeast cells in media in the absence of tryptophan, uracil, and histidine. The yeast cells being cultured carry the following: (1) a reporter construct comprising one or more copies, preferably eight copies, of the LexA operon fused to a gene encoding lacZ, i.e., a lacZ reporter gene downstream of eight copies of the LexA operon; (2) a gene encoding the RSV matrix protein fused to the LexA DNA binding domain under the control of a full length ADH1 promoter; and (3) a gene encoding the RSV matrix protein fused to the B42 protein activation domain under the control of a GAL1 promoter. The second step is to measure the induction of the reporter lacZ gene in the yeast cells in culture with an increase in lacZ enzyme activity indicating the presence of RSV matrix protein interaction. In the third step, a test sample is added to the yeast cell culture and the effect of the test sample on lacZ enzyme activity is measured, with a decrease in lacZ enzyme activity indicating the test sample inhibits RSV matrix protein interaction and an increase in lacZ enzyme activity indicating the test sample promotes RSV matrix protein interaction.

The yeast cells are transformed and cultured using the techniques described previously. The reporter construct can be readily made using the information given above or is available from the Clontech MATCHMAKER™ LexA two hybrid system, Clontech Laboratories, Inc., Palo Alto, Calif. The first and second genes can be made by cloning the entire RSV M gene or any suitable RSV matrix protein gene into pLexA and pB42AD expression plasmids, as described more fully in Example 3. The pLexA and pB42AD expression plasmids are available from the Clontech MATCHMAKER™ LexA two hybrid system, Clontech Laboratories, Inc., Palo Alto, Calif. The ADH1 promoter in the pLexA expression plasmid and the GAL1 promoter in the pB42AD expression plasmid are described in Feilotter, H. E., et al., (1994) Nucleic Acids Res., 22: 1502–1503. A sample of E. coli (DH5α) containing the gene encoding the RSV matrix protein fused to the LexA DNA binding domain in accordance with the present invention, designated E. coli DH5α LexA-M, has been deposited under the terms of the Budapest Treaty with the American Type Culture Collection (ATCC) at 12301 Parklawn Drive, Rockville, Md. 20852 USA under Accession Number ATCC 98322. A sample of E. coli (DH5α) containing the gene encoding the RSV matrix protein fused to the B42 protein activation domain in accordance with the present invention, designated E. coli DH5α pB42-M, has been deposited under the terms of the Budapest Treaty with the American Type Culture Collection (ATCC) at 12301 Parklawn Drive, Rockville, Md. 20852 USA under Accession Number ATCC 98323.

The presence of RSV matrix protein interaction is determined by measuring lacZ (β- galactosidase) activity of the transformed cultured yeast cells. The transformed yeast cell cultures are streaked onto galactose synthetic dropout medium (minus tryptophan, uracil and histidine) and incubated for three days at 30° C. After the three day incubation period, a colony-lift filter assay is performed to determine β-galactosidase activity. The presence of blue colonies indicates a positive reaction, meaning that RSV matrix protein—protein interaction was indicated by the induction of the reporter lacZ gene resulting in the formation of blue color in the colonies. The absence of blue color formation would indicate that there was no induction of the reporter lacZ gene and therefore no interaction had occurred between the two hybrid proteins.

In another preferred method of screening for inhibitors of RSV matrix protein interaction, the first step comprises expressing RSV matrix protein, preferably human RSV matrix protein, in E. coli as a maltose binding protein (MBP) fusion which is purified by an amylose affinity column. In the second step, fusion RSV matrix protein-MBP is further purified by size exclusion chromatography and the amount of monomers and dimers of the fusion RSV matrix protein-MBP are measured. Monomers (70 kDa) and dimers (140 kDa) are measured as protein elution peaks at 200 nm obtained from size exclusion chromatography. The third step comprises adding a test sample to the purified fusion RSV matrix protein-MBP and measuring the effect on formation of monomers and dimers by measuring protein elution peaks at 220 nm obtained from size exclusion chromatography as described above. An increase in the amount of monomers indicates the test sample inhibits RSV matrix protein interaction. An increase in dimer or multimer formation indicates that the test sample promotes RSV matrix protein interaction.

In order that this invention may be better understood, the following examples are set forth. The examples are for the purposes of illustration only and are not to be construed as limiting the scope of the invention.

EXAMPLE 1

Expression of Human Respirator Syncytial Virus (RSV) Matrix Protein in E. coli

The entire coding sequence, antigenomic message sense, of RSV matrix protein (M) was amplified by polymerase chain reaction (PCR) using the RSV 2B viral genome as template and the following primers:
5'--CGGAATTCATGGAAACATACGTGAACAAGCTT-3' (forward) (SEQ ID NO: 7), and
5'--AGGGCCCTAGGTTAATCCTCTAGTGGTTT-3' (reverse) (SEQ ID NO: 8).

The PCR-amplified M gene (792 base pairs) (described in Satake, M. and Venkatesan, S., (1984) J. Virol., 50:92–99) was engineered to possess an EcoRI and a BamHI restriction site at the 5' and 3' ends respectively with an in frame stop codon in front of the BamHI site. The resulting M gene, which was confirmed by sequencing, was inserted into the EcoRI and BamHI restriction sites of the pMAL-c expression vector (New England Biolabs, Beverly, Mass.) for the expression of an in frame maltose binding protein-M fusion. The fusion construct (pMAL-M) was used to transform *E. coli* strain BL21. Soluble fusion protein (MBP-M) was prepared from isopropyl-1-thio-β-D-galactopyranoside (IPTG)-induced BL21 cells.

Soluble extracts of the MBP-M fusion protein containing 5 mg protein were loaded onto an amylose affinity column (2 ml bed volume) and purified by chromatography according to the manufacturer's instructions (New England Biolab). Briefly, the soluble extract in column buffer (10 mM phosphate, 0.5 M sodium chloride, 1 mM sodium azide, 10 mM β-mercaptoethanol and 1 mM EGTA, pH 7.0) was applied to an amylose resin affinity column. After the column was washed with column buffer to remove the unbound fractions, the fusion protein was eluted stepwise from the column with 10 mM maltose.

The first three ml fractions were collected and concentrated to 200–400 μl with a Centricon-50 (Amicon). Aliquots (20 μl) of this concentrated sample were treated with the protease Factor Xa (New England Biolabs, Beverly, Mass.) which cleaves at the site immediately after the sequence ile-glu-gly-arg at a w/w ratio of 1–2% of the amount of the fusion protein in order to separate the M matrix protein from the maltose binding protein (MBP) by cleaving the affinity-purified fusion protein. Other 20 μl aliquots were not treated with factor Xa. Aliquots (20 μl) of the concentrated sample in the absence (lane 1) or presence (lane 2) of Factor Xa treatment were resolved on a12% SDS-PAGE and the gel was stained with Coomassie blue. The fusion protein had a molecular mass of 70 kD (FIG. 1A, lane 1). The minor band with a molecular mass of 40 kD is a contaminant co-eluted with the fusion protein. When the fusion protein was treated with the protease Factor Xa, MBP was partially cleaved from the M protein which had a molecular mass of 30 kD (FIG. 1A, lane 2).

Figure 1B:
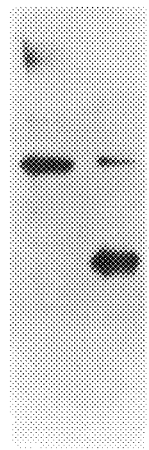
FIG. 1(B) is a Western blot of affinity-purified MBP-M fusion protein probed with a polyclonal antibody raised against purified MBP. All molecular weight standards are in kilodaltons (kD).

Western blot analysis using a polyclonal antibody against the MBP confirmed that the 70 kD protein is indeed the MBP-fusion protein (FIG. 1B, lane 1). Affinity-purified MBP-M fusion proteins in the absence (lane 1) or presence (lane 2) of Factor Xa treatment were resolved by 12% SDS-PAGE. Proteins were transferred onto a nitrocellulose membrane, which was probed with a polyclonal antibody raised against purified MBP (New England Biolab). The second antibody was goat anti-rabbit (IgG) conjugated with horseradish peroxidase (Bio-Rad, Hercules, Calif., USA). All molecular weight standards are indicated in kD (kilodalton). After Factor Xa treatment, most of the 70 kD protein was converted into MBP with a molecular mass of 43 kD (FIG. 1B, lane 2). There was no cross reactivity between the antiserum and the RSV M protein.

Approximately 60% of the MBP-M fusion protein was in soluble form and the expression level of the fusion protein was estimated to be 40–50 mg/liter of culture. The MBP-M fusion protein from the soluble extracts could be purified to a great extent, as high as 80%, in a single step using an amylose affinity column as revealed by SDS-PAGE.

EXAMPLE 2

Homodimer Formation and Multimerizaton of RSV Matrix Protein (M)

Size exclusion chromatography experiments utilized a 1 cm×30 cm Superose 12 column (Pharmacia Biotech) eluted with 0.1M ammonium bicarbonate buffer at a flow rate of 1 ml per minute. Routinely, 25 to 100 μl of sample were injected into the column and fractions were collected at 0.25 ml intervals. Detection of protein elution peaks was performed at 220 nm. The sizing characteristics of the column were calibrated by a series of protein standards including Apoferritin from horse spleen (443 kD), β-Amylase from sweet potato (200 kD), bovine serum albumin (67 kD), ovalbumin (45 kD), and soybean trypsin inhibitor (20 kD), which were obtained from Sigma Chemical Company. A linear standard curve was generated by plotting the log of molecular weight versus the elution volume of each standard. The void volume of the column was 7 ml which corresponds to a molecular cutoff of 2000 kD. The relative molecular weights of various experimental peaks were determined by comparison to this standard curve.

SDS-PAGE analysis of size exclusion column fractions was carried out on a Pharmacia Phast system on precast 8–25% gradient acrylamide gels and silver stained in the same instrument using the standard protocol of the Pharmacia PhastGel Silver kit. Sample volumes ranged from 1 to 4 μl. A Sigma low molecular weight markers kit was used for gel calibration.

In this example, concentrated affinity-purified MBP-M (100 μl) was injected into a 1 cm×30 cm Superose 12 column, which was equilibrated and eluted with 0.1M ammonium bicarbonate buffer. Fractions were collected at 0.25 ml intervals. Detection of protein elution peaks was performed at 220 nm. Aliquots (5 μl) of the fractions collected in the void volume and the starting material prior to column chromatography were resolved by 12% SDS-PAGE and the gel was subjected to silver staining as described above.

Figure 2A:
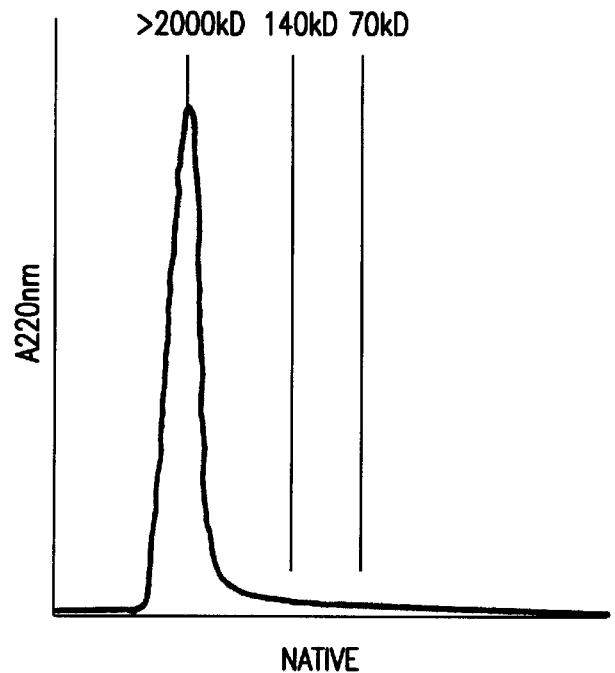
FIG. 2(A) is a graph depicting the molecular weights in kilodaltons (kD) of protein elution peaks of native MBP-M protein detected at 220 nm.

When the affinity-purified MBP-M fusion protein was injected into a Superose 12 column, one major elution peak was present in the void volume, which has a molecular mass of >2000 kD (FIG. 2A). This sample contained the MBP-M as indicated by SDS-PAGE, indicating that the affinity-purified MBP-M formed high molecular weight aggregates. In order to dissociate these aggregates for further analysis on Superose 12, the affinity-purified fusion protein was adjusted to 7.5M urea, diluted to 3.75M urea, and immediately injected into the column.

Aliquots (100 μl) of the same sample as described for FIG. 2A were adjusted to 7.5M urea prior to Superose 12 column chromotography. Fractions were collected for SDS-PAGE analysis as described previously which consisted of starting material; void volume; and fractions collected between 140 kD and 70 kD elution peaks. Molecular weights standards of 14 kD, 20 kD, 24 kD, 29 kD, 36 kD, 45 kD, and 67 kD were employed in the SDS-PAGE analysis.

Figure 2B:
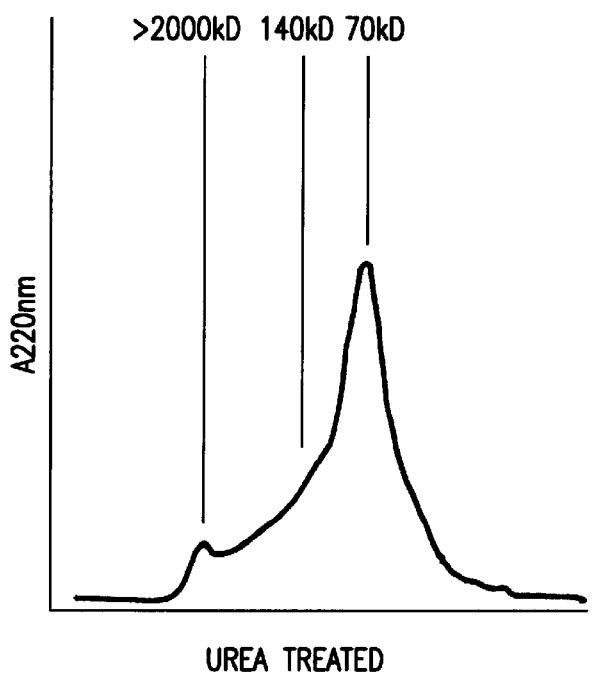
FIG. 2(B) is a graph depicting the molecular weights in kilodaltons (kD) of protein elution peaks of urea-treated affinity-purified MBP-M protein detected at 220 nm.

As indicated in FIG. 2B, the elution peak shifted from the void volume to the 70 kD position with a broad shoulder at the 140 kD position. Silver-staining of the SDS-PAGE revealed that fractions collected for this peak and its shoulder contained highly purified 70 kD protein. The identification of this 70 kD protein as MBP-M fusion protein was confirmed by Western blot analysis, indicating the presence of monomeric forms of the MBP-M fusion protein in the 70 kD peak and dimeric forms of the MBP-M fusion protein in the shoulder.

In order to further examine homodimer formation, the affinity-purified MBP-M fusion protein was analyzed on a Superose 12 column following different periods of incubation in 3.75M urea. Aliquots (100 μl) of concentrated affinity-purified MBP-M were treated with 7.5M urea as described previously and then diluted to 3.75M urea. One sample was injected immediately into a Superose 12 column (designated as time zero). Two other samples were incubated in the diluted urea for 30 minutes prior to column chromatography. Protein elution peaks for high molecular aggregates (>2000 kD), 140 kD and 70 kD were detected at 220 nm.

Figure 3:
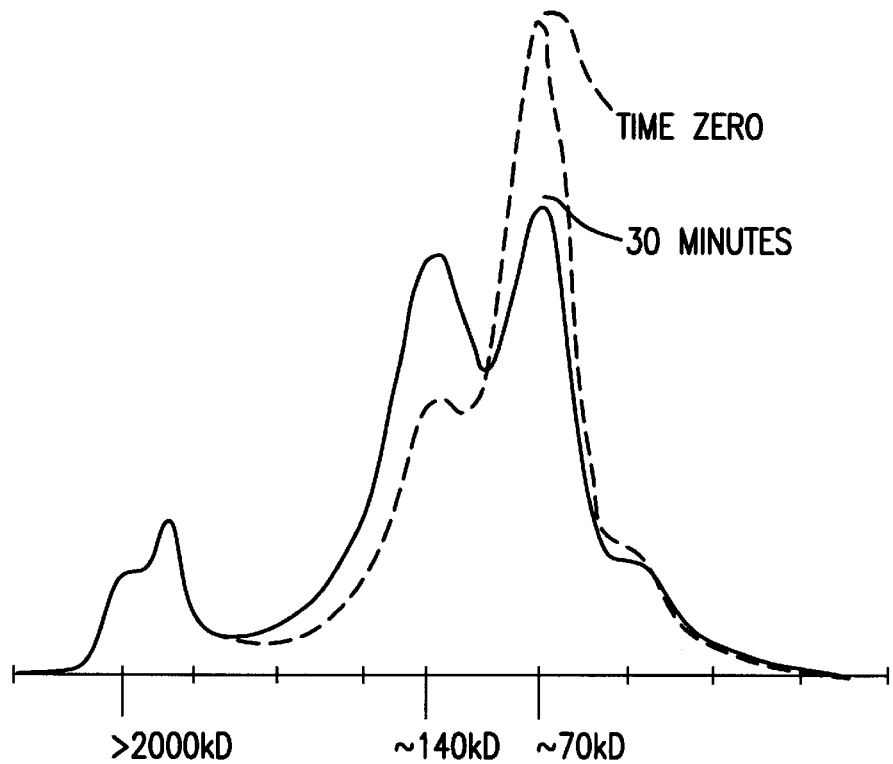
FIG. 3, is a graph depicting the molecular weights in kilodaltons (kD) of protein elution peaks detected at 220 nm of affinity-purified MBP-M protein treated with 7.5M urea and then diluted to 3.75M urea. One sample was injected immediately into a Superose 12 column which is designated as "Time Zero" in the graph. Two other samples were incubated in the diluted urea for 30 minutes prior to column chromatography which are designated "30 Minutes" in the graph.

When the sample was adjusted to 3.75M urea and injected into the column immediately, a sharp elution peak at 70 kD and a small shoulder at 140 kD were detected (FIG. 3). After 30 minutes incubation in 3.75M urea, approximately half of the 70 kD peak was shifted to the 140 kD peak. After 60 hours incubation, the major peak shifted to the 140 kD position with a small shoulder at 70 kD (data not shown). Some of the fusion proteins were also present in the void volume as aggregates. SDS-PAGE analysis of the fractions collected at the void volume, 140 kD and 70 kD elution peaks, revealed that they were MBP-M fusion proteins, further supporting the observation that the MBP-M fusion protein forms homodimers and higher-level multimers in vitro.

Figure 4:
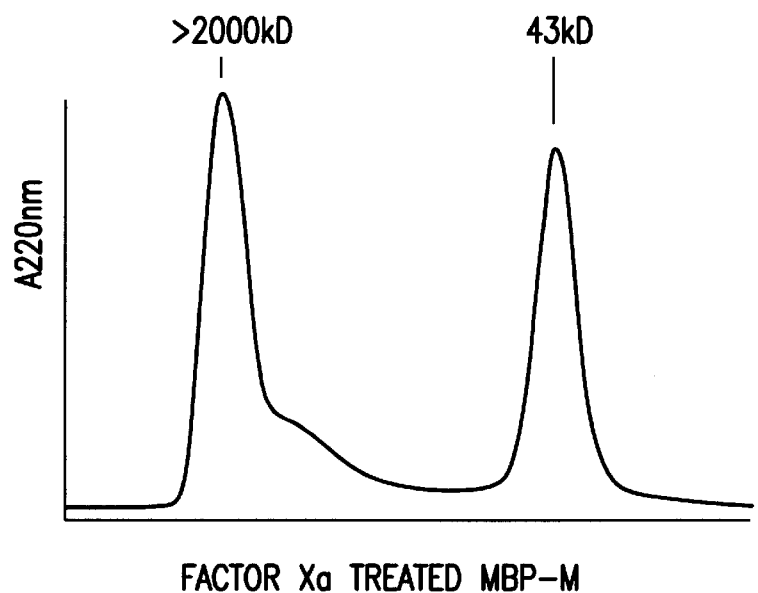
FIG. 4 is a graph depicting the molecular weights in kilodaltons (kD) of protein elution peaks detected at 220 nm of affinity-purified MBP-M protein treated with Factor Xa prior to Superose 12 column chromatography.

In order to rule out the possibility that homodimer formation of the fusion protein was due to MBP, a sample of the affinity-purified fusion protein was cleaved by Factor Xa and injected into a Superose 12 column in the absence of urea. Specifically, an aliquot (100 μl) of affinity-purified MBP-M was treated with Factor Xa prior to Superose 12 column chromatography. Protein elution peaks were detected at 220 nm as shown in FIG. 4. Aliquots (5 μl) of the starting materials, the fraction collected for the void volume, and the fractions collected for the 43 kD elution peak were analyzed by 12% SDS-PAGE and the proteins were visualized by silver stain. Molecular weight standards used in the SDS-PAGE were 14 kD, 20 kD, 24 kD, 29 kD, 36 kD, 45 kD, and 67 kD. Aliquots (30 μl) of fractions collected for the void volume and the 43 kD elution peaks were analyzed by Western blot using a polyclonal antiserum against purified MBP. The protein elution profiles showed two major peaks, one at the void volume (>2,000 kD) and the other at 43 kD as shown in (FIG. 4). Analysis of the void volume by silver staining of material separated on SDS acrylamide gel revealed two major bands corresponding to MBP-M fusion protein and the M protein, whereas the fraction collected for the 43 kD peak contained a highly purified MBP. The presence of the fusion protein and the MBP in the void volume and the 43 kD elution peak, respectively, was confirmed by Western blot analysis. The foregoing data clearly indicate that MBP neither forms a homodimer nor associates with the M protein and that homodimer formation of the fusion protein is due to the RSV M protein per se.

EXAMPLE 3

Specific Protein—Protein Interaction Between RSV M Protein In Vivo

To express in frame fusion proteins encoding M with the GAL4 DNA-binding domain or the GAL4 activation domain, the PCR-amplified M gene described previously in Example 1 was inserted into the EcoRI and BamHI restriction sites of the yeast two hybrid expression plasmids, pGBT$_9$ and pGAD$_{424}$ (Feilotter, H. E., et al., (1994) Nucleic Acid Res., 22:1502–1503). The resulting expression plasmids, pGBT$_9$-M (GAL4 DNA-binding domain fused to M protein) and pGAD$_{424}$-M (GAL4 activation domain fused to M protein) were used to transform the Saccharomyces cerevisiae yeast strain, HF7c (MATa ura3-52, his3-200, lys2-801, ade2-101, trp1-901, leu2-3, 112 gal4-542, gal80-538, LYS2::GAL1UAS-HIS3, URA3::GAL4-lacZ) (Feilotter, H. E., et al., (1994) Nucleic Acids Res., 22:1502–1503). Growth and transformation of yeast cells were performed according to standard procedures (Sherman, F., et al., (1982) Methods in Yeast Genetics: a Laboratory Manual, Cold Spring Harbor Laboratory, NY). Double transformant yeast strains were grown in synthetic drop-out medium to maintain expression plasmids. Expression of GAL4 fusion proteins was under the control of the ADH1 promoter (Feilotter, H. E., et al., (1994) Nucleic Acids Res., 22:1502–1503).

To demonstrate the specificity of M/M interaction, other GAL4 fusion proteins, including the human BAX protein which belongs to the BC12 family involved in programmed cell death (Thomas, W. S., et al., (1995) Proc. Natl. Acad. Sci. USA, 92:7834–7838), and the intracytoplasmic domains of the RSV F and G glycoproteins were examined for their interaction with M protein. Briefly, the human BAX coding sequence was cloned into the two yeast expression plasmids as described previously to generate the two fusion constructs (GBT$_9$-BAX and GAD$_{424}$-BAX) (see Table 1) (Thomas, W. S., et al., (1995) Proc. Natl. Acad. Sci. USA, 92:7834–7838). For the expression of in frame fusion proteins containing the GAL4 activation domain fused to the intracytoplasmic domains of RSV fusion protein (F) (Collins, P. L., et al., (1984) Proc. Natl. Acad. Sci. USA, 81:7683–7687) or G glycoprotein (Wertz, G. W., et al., (1985) Proc. Natl. Acad. Sci. USA, 82:4075–4079), annealed oligonucleotides containing the last 24 amino acids from the C-terminus of F protein or the first 41 amino acids from the N-terminus of G glycoprotein were inserted into SmaI and BamHI restriction sites of the yeast expression plasmid, GAD$_{424}$. Different combinations of these fusion constructs were used to transform HF7c yeast strains, which carry the HIS3 reporter gene under the control of the GAL1 promoter (Feilotter, H. E., et al., (1994) Nucleic Acids Res., 22:1502–1503), and the resulting double-transformant yeast strain (S. cerevisiae GBT-M+GAD-M) were examined for their growth phenotypes on selective medium. A sample of the resulting double-transformant yeast strain S. cerevisiae GBT-M+GAD-M has been deposited under the terms of the Budapest Treaty with the American Type Culture Collection (ATCC) at 12301 Parklawn Drive, Rockville, Md. 20852 USA under Accession Number ATCC 74401.

Specific protein—protein interaction was identified by growth of the double-transformants on selective medium lacking tryptophan, leucine, and histidine as described in Table 1. As shown in Table 1, BAX—BAX and M—M exhibited strong protein—protein interactions as reflected by the ability of the yeast strains (GBT$_9$-BAX+GAD$_{424}$-BAX and GBT$_9$-M+GAD$_{424}$-M) to grow on selective medium lacking tryptophan, leucine and histidine. This example demonstrates that these protein—protein interactions are highly specific within the complex milieu of the cell. This example also demonstrates that BAX protein does not interact with M protein nor do either of these proteins interact with the intracytoplasmic domains of RSV F or G proteins.

TABLE 1

INTERACTIONS BETWEEN M, F, AND G PROTEINS OF RSV IN THE YEAST TWO HYBRID ASSAY

|  | GBT$_9$-BAX | GBT$_9$-M |
|---|---|---|
| GAD$_{424}$-BAX | +++ | – |
| GAD$_{424}$-M | – | ++ |
| GAD$_{424}$-F | – | – |
| GAD$_{424}$-G | – | – |

The yeast strain (HF7c) was transformed with the fusion plasmids as indicated above in Table 1. GBT$_9$-BAX and GBT$_9$-M are the plasmids expressing GAL4 DNA-binding domains fused in frame with the human Bax and RSV Matrix protein, respectively. GAD$_{424}$-BAX, GAD$_{424}$-M, GAD$_{424}$-F and GAD$_{424}$-G are the GAL4 activation domains fused in frame with the human Bax, RSV Matrix protein, cytoplasmic domain of RSV fusion protein (F), and cytoplasmic domain of RSV G glycoprotein, respectively. Growth phenotype of double transformant yeast strains was examined on selective medium lacking tryptophan, leucine and histidine after 4 days incubation at 30° C. No growth is indicated by (–), whereas the intensity of growth observed is indicated by (++) and (+++).

EXAMPLE 4

Mapping the Domains for M—M Interaction in the Yeast Two Hybrid Assay

In order to map the interaction domains between RSV M proteins, six C-terminal deletion mutants (M1, M2, M3, M5, M6 and M7) were constructed by PCR using the M gene described previously in Example 1 as a template. The amino acid sequences deleted from the C-terminal of the RSV M protein to make the M1, M2, M3, M5, M6, and M7 are set forth in, respectively, SEQ ID NO:3, SEQ ID NO:2, SEQ ID NO:1, SEQ ID NO:4, SEQ ID NO:5, and SEQ ID NO: 6. All of these mutants, which contained unique SmaI and BamHI restriction sites at the 5' and 3' ends, respectively, with an in frame stop codon in front of the BamHI restriction site, were cloned into the pGAD$_{424}$ expression plasmid of Example 3 to produce in frame GAL4 activation domain fusion constructs designated GAD-M1, GAD-M2, GAD-M3, GAD-M5, GAD-M6, and GAD-M7, as shown in FIG. 5. Mutant M4, which consists of a double stranded oligonucleotide encoding the last 28 amino acids of the M gene, was cloned into pGBT$_9$ and pGAD$_{424}$ expression plasmids and designated GBT-M4 and GAD-M4, respectively, as shown in FIG. 5.

Yeast strains carrying the GBT-M4 expression vector were transformed with each of the GAL4 activation domain (GAD) fusion constructs as described in Example 3. The double transformant yeast strains were tested for their growth phenotypes on selective medium lacking tryptophan, leucine, and histidine. The ability of the yeast strain to grow on this medium was interpreted as positive (+) for protein—protein interaction.

The following primers were used for PCR amplification to make the m protein mutants designated M1, M2, M5, M6, and M7:
Forward primers:5'-GGGAATGGAAACATACGTGAACAAGCTT-3'(SEQ ID NO:9)

Reverse primers:
M1:5'-CGGGATCCTTAAACTGTGATAACTAACACTA-3'(SEQ ID NO:10)
M2:5'-CGGGATCCTTAGTAGGCACCAAGATCTACTA-3'(SEQ ID NO:11)
M3:5'-CGGGATCCTTATTCGGTGGTTGCTATATTTC-3+(SEQ ID NO:12)
M5:5'-CGGGATCCTTATATTACTCTTTTTGATGTCAT-3' (SEQ ID NO:13)
M6:5'-CGGGATCCTTATTTGATTTCACAAGGTGTAG-3'(SEQ ID NO:14)
M7:5'-CGGGATCCTTAGATGAAATTACTAGGCATTT-3' (SEQ ID NO:15)

Fusion constructs containing the seven deletion mutants, described above and shown in FIG. 5, fused to the GAL4 activation domain (GAD$_{424}$) were used to transform HF7c yeast strains, which carried either an empty GBT$_9$ expression vector or an expression vector for mutant M4 (GBT-M4). The interaction between M4 and the C-terminal deletion mutants was examined by analyzing the growth phenotype of the double transformant yeast strains on selective medium lacking tryptophan, leucine, and histidine. As shown in FIG. 5, M4 (GBT-M4) interacted with the wild type M gene (GAD-M), M3 (GAD-M3), M2 (GAD-M2), and M1 (GAD-M1). These protein—protein interactions were abolished when the fusion construct, GBT-M4 was replaced by the empty vector, GBT$_9$ (data not shown). Mutants M5 (GAD-M5), M6 (GAD-M6), and M7 (GAD-M7) did not interact with M4. Furthermore, M4 (GBT-M4) did not interact with itself (GAD-M4). No protein—protein interaction between M3/M3 , M2/M2 and M1/M1 could be detected (data not shown). The data indicated that the last twenty-eight amino acids at the C-terminus and an internal region (amino acids 160–183) of the M proteins are important for their interactions. Based on the data in FIG. 5, the amino acids at positions 160 to 183 of the M protein that interact with the C-terminus of the RSV matrix protein are: IleProThrTyrLeuArgSerIleSer-ValLysAsnLysAspLeuAsnSerLeuGluAsnIleAlaThr ThrGlu (SEQ ID NO:16).

EXAMPLE 5

Yeast-Based Screening Assay

The double transformant yeast strain which carried the Gal4 fusion plasmids (GBT-M and GAD-M) was grown in synthetic drop-out medium lacking tryptophan, leucine, and histidine. The ingredients of this selective medium contained 2% dextrose, 0.67% yeast nitrogen base without amino acids, and the following amino acids: adenine sulfate, uracil, L-arginine, L-methionine, L-tyrosine, L-isoleucine, L-lysine, L-phenylalanine, L-glutamic acid, L-aspartic acid, L-valine, L-threonine and L-serine. Another yeast strain which carried the Gal4-Bax fusion plasmids was used as a control in this screen (Thomas, W. S., et al., (1995), Proc. Natl. Acad. Sci. USA, 92:7834–7838). Briefly, the entire human BAX gene without the last twenty amino acids at the C-terminus was amplified by PCR using B-cell lymphocyte cDNA as a template. The resulting BAX gene, which contained a unique SmaI at the 5' end and a BamHI at the 3' end, was cloned into the yeast two hybrid expression plasmids, pGBT and pGAD, as described previously.

When yeast cells were grown to an optical density (OD) of 1.0 at 600 nm, the culture was diluted (1:80) with selective medium having an OD of 0.05 at 600 nm. 200 µl of these diluted yeast cell cultures were dispensed into a 96 well plate which contained the test samples in amounts of 100 ng per well. The OD of yeast cultures from these plates were taken using a robot after being incubated for 24 hours at 30° C. and normally ranged from 0.4 to 0.6 without the presence of any test sample. Compounds were scored to be potential inhibitors for RSV M protein when they inhibited normal cell growth by more than 50%. Concurrently, the specificity of this inhibition was confirmed by testing the same compounds on the control yeast strain which carried the Gal4-Bax fusion plasmids. Compounds which inhibited cell growth of both yeast strains were considered to be toxic (antifungal) to yeast cells and would be discarded. By the same token, compounds which enhance the growth of the yeast strain expressing Gal4-matrix protein fusion but not the Gal4-Bax fusion protein would be exploited as potential promoters for matrix—matrix protein interaction.

EXAMPLE 6

LexA Two Hybrid Yeast-Based Screening Assay

This screening assay used triple transformant yeast strains to identify inhibitors or promoters of RSV matrix protein interaction. The pLexA and pB42AD expression plasmids of the LexA two hybrid system (Clontech Laboratories, Inc., Palo Alto, Calif.) and a lacZ reporter plasmid were employed in making the triple transformant yeast strains. In order to clone the entire RSV M gene into the pLexA and pB42AD expression plasmids, the BamHI site of the GBT-M plasmid of Example 3 was replaced by a unique XhoI site in order to remove the M gene by double digestion of EcoRI and XhoI sites. The resulting plasmid was digested with EcoRI and XhoI to release the entire M gene, which was subsequently inserted into the EcoRI and XhoI sites of both the pLexA and pB42AD expression plasmids. The resulting LexA fusion plasmid (pLexA-M) expressed *E. coli* LexA DNA-binding domain fused to the M gene under the control of a full length ADH1 promoter (available from Clontech Laboratories, Inc., Palo Alto, Calif.). The pB42AD fusion plasmid (pB42AD-M) expressed B42 protein activation domain fused to the M gene under the control of a GAL1 promoter. The shuttle vector contained the yeast 2 micron plasmid, an origin for DNA replication, an ampicillin-resistant gene, and a auxotrophic marker (HIS3). The pB42AD fusion plasmid (pB42AD-M) expressed B42 protein activation domain fused to the M gene under the control of a GAL1 promoter. This vector has the same backbone, except that the auxotrophic marker is TRP1. These fusion plasmids were used to transform EGY48 yeast strain (Clontech Laboratories, Inc., Palo Alto, Calif.), which carried the lacZ reporter plasmid (p8op-lacZ) upstream of 8 copies of the LexA operon (Ebina, Y., et al., (1983) *J. Biol. Chem.*, 258:13258–13261). The triple transformant yeast strains (*S. cerevisiae* LexA-M+pB42-M) were selected by tryptophan, uracil and histidine auxotrophy. A sample of the resulting triple-transformant yeast strain *S. cerevisiae* LexA-M+pB42-M has been deposited under the terms of the Budapest Treaty with the American Type Culture Collection (ATCC) at 12301 Parklawn Drive, Rockville, Md. 20852 USA under Accession Number ATCC 74400.

To test for the presence of M—M protein interaction in the LexA two hybrid system, triple transformant yeast strains carrying different combinations of the fusion plasmids were streaked onto galactose synthetic dropout medium (minus tryptophan, uracil and histidine) and incubated for three days at 30° C. After the three day incubation period, a colony-lift filter assay was performed to determine β-galactosidase activity in accordance with the manufacturer's instructions (Clontech Laboratories, Inc., Palo Alto, Calif.). Briefly, yeast colonies (1 to 2 mm in diameter) were transferred to the filter. The filter which contained yeast colonies was submerged in a pool of liquid nitrogen, for about 5 seconds, and subsequently thawed at room temperature. The filter was then placed on another filter which had been presoaked in Z-buffer/X gal solution and incubated at 30° C. for 30 minutes to several hours. The presence of blue colonies indicated a positive reaction. Protein—protein interaction was indicated by the induction of the reporter lacZ gene which resulted in the formation of blue color in the colonies, whereas the absence of blue color formation indicated that there was no induction of the reporter lacZ gene and therefore no interaction occurred between the two hybrid proteins.

Subsequently, a test sample is added to the yeast cell culture containing the selected triple transformant yeast cells and the effect on enzyme activity is measured, wherein inhibition of enzyme activity indicates the test sample inhibits RSV matrix protein interaction and enhancement of enzyme activity indicates the test sample promotes RSV matrix protein interaction.

---

We claim:

1. A method of screening for modulators of respiratory syncytial virus (RSV) matrix protein interaction comprising the steps of:
 (a) culturing a host cell carrying a nucleic acid sequence coding (1) an RSV matrix protein or an N-terminal fragment of said RSV matrix protein having at least 183 amino acids fused to (2) a protein selected from the group consisting of maltose binding protein (MBP) and glutathione-S-transferase;
 (b) expressing said fused RSV matrix protein or said fused RSV matrix protein fragment in the cultured host cell of step (a);
 (c) measuring the interaction of said fused RSV matrix protein or fused RSV matrix protein fragment expressed in step (b); and
 (d) adding a test sample to said expressed fused RSV matrix protein or expressed fused RSV matrix protein fragment of step (c) and measuring the effect on RSV matrix protein interaction, wherein an increase in the RSV matrix protein interaction indicates the test sample promotes RSV matrix protein interaction and a decrease in the RSV matrix protein interaction indicates the test sample inhibits RSV matrix protein interaction.

2. The method of claim 1, wherein the nucleic acid sequence carried by the cultured host cell of step (a) encodes an RSV matrix protein fused to MBP.

3. The method of claim 1, wherein the nucleic acid sequence carried by the cultured host cell of step (a) encodes an N-terminal fragment of an RSV matrix protein having at least 183 amino acids fused to MBP.

4. The method of claim 1, wherein the RSV matrix protein interaction is measured in step (c) by measuring the amount of formation of monomers and dimers of the fusion RSV matrix protein-MBP or fusion RSV matrix protein fragment-MBP and the effect of the test sample added in step (d) is measured by the effect on the amount of formation of monomers and dimers, wherein an increase in the amount of monomers indicates the test sample inhibits RSV matrix protein interaction.

5. A method for screening for modulators of RSV matrix protein interaction comprising the steps of:
 (a) culturing yeast cells carrying: (1) a reporter construct comprising a promoter fused to an open reading frame encoding a reporter, (2) a gene encoding a transcription factor for the reporter of step (a)(1) having a DNA binding domain fused to a RSV matrix protein or to an N-terminal fragment of said RSV matrix protein having at least 183 amino acids, and (3) a gene encoding a transcription factor for the reporter of step (a)(1) having an activation domain fused to a RSV matrix protein or to an N-terminal fragment of said RSV matrix protein having at least 183 amino acids;
 (b) measuring the amount of expression of the reporter of step (a)(1) in the yeast cell culture of step (a), wherein an increase in the amount of expression of the reporter of step (a)(1) indicates the presence of RSV matrix protein interaction; and
 (c) adding a test sample to the yeast cell culture of step (b) and measuring the effect of the test sample on the amount of expression of the reporter of step (a)(1) in the yeast cell culture of step (b), wherein inhibition of the amount of expression of the reporter of step (a)(1) indicates the test sample inhibits RSV matrix protein interaction and enhancement of the amount of expression of the reporter of step (a)(1) indicates the test sample promotes RSV matrix protein interaction.

6. The method of claim 5, wherein the reporter construct of step (a)(1) comprises a GAL1 promoter fused to a gene encoding His3.

7. The method of claim 5, wherein the gene of step (a)(2) encodes a GAL4 DNA binding domain fused to said RSV matrix protein or said N-terminal fragment of said RSV matrix protein, and the gene of step (a)(3) encodes a GAL4 activation domain fused to said RSV matrix protein or said N-terminal fragment of said RSV matrix protein.

8. The method of claim 7, wherein the gene of step (a)(2) encodes the GAL4 DNA binding domain fused to a C-terminal fragment of the RSV matrix protein comprising the amino acid sequence of SEQ ID NO:1.

9. The method of claim 8, wherein the gene of step (a)(2) is on an expression vector designated GBT-M (ATCC Accession No. 98327).

10. The method of claim 8, wherein the gene of step (a)(3) encodes the GAL4 activation domain fused to an N-terminal fragment of said RSV matrix protein having at least 183 amino acids, which N-terminal fragment can bind to said C-terminal fragment of the RSV matrix protein encoded by the gene of step (a)(2).

11. The method of claim 10, wherein said N-terminal fragment of said RSV matrix protein encoded by the gene of step (a)(3) is selected from the group consisting of RSV matrix protein fragments designated GAD-M3, GAD-M2, and GAD-M1.

12. The method of claim 8, wherein the gene of step (a)(3) is on an expression vector designated GAD-M (ATCC Accession NO. 98326).

13. The method of claim 7, wherein the gene of step (a)(3) encodes the GAL4 activation domain fused to a C-terminal fragment of the RSV matrix protein comprising the amino acid sequence of SEQ ID NO:1.

14. The method of claim 13, wherein the gene of step (a)(2) encodes the GAL4 binding domain fused to an N-terminal fragment of said RSV matrix protein having at least 183 amino acids, which N-terminal fragment can bind to said C-terminal fragment of said RSV matrix protein encoded by the gene of step (a)(3).

15. The method of claim 14, wherein said N-terminal fragment of said RSV matrix protein encoded by the gene of step (a)(3) is selected from the group consisting of RSV matrix protein fragments designated GAD-M3, GAD-M2, and GAD-M1.

16. The method of claim 5, wherein the cultured yeast cells are *Saccharomyces cerevisiae*.

17. The method of claim 5, wherein the reporter construct of step (a)(1) comprises a GAL1 promoter fused to a gene encoding His3; the gene of step (a)(2) encodes a GAL4 DNA binding domain fused to said RSV matrix protein, and the gene of step (a)(3) encodes a GAL4 activation domain fused to said RSV matrix protein.

18. The method of claim 17, wherein the cultured yeast cells of step (a) are the yeast cells designated *Saccharomyces cerevisiae* GBT-M+GAD-M (ATCC Accession No. 74401).

19. A method of screening for modulators of RSV matrix protein interaction comprising the steps of:
   (a) culturing yeast cells carrying: (1) a reporter construct comprising from one to eight copies of a LexA operon fused to a gene encoding lacZ, (2) a gene encoding an RSV matrix protein or an N-terminal fragment of said RSV matrix protein having at least 183 amino acids fused to a LexA DNA binding domain under the control of a full length ADH1 promoter, and (3) a gene encoding an RSV matrix protein or an N-terminal fragment of said RSV matrix protein having at least 183 amino acids fused to the B42 protein activation domain under the control of a GAL1 promoter, in selective media;
   (b) measuring the effect on lacZ enzyme activity of the cultured yeast cells of step (a), wherein an increase in lacZ enzyme activity indicates the presence of RSV matrix protein interaction; and
   (c) adding a test sample to the yeast cell culture of step (b) and measuring the effect of the test sample on lacZ enzyme activity, wherein a decrease in lacZ enzyme activity indicates the test sample inhibits RSV matrix protein interaction and an increase in lacZ enzyme activity indicates the test sample promotes RSV matrix protein interaction.

20. The method of claim 19, wherein the gene of step (a)(2) is on an expression vector designated LexA-M (ATCC Accession No. 98322).

21. The method of claim 19, wherein the gene of step (a)(3) is on an expression vector designated pB42-M (Accession No. 98323).

22. The method of claim 19, wherein the cultured yeast cells of step (a) are the yeast cells designated *Saccharomyces cerevisiae* LexA-M+pB40-M+1 and 2 (ATCC Accession No. 74400).

* * * * *